United States Patent [19]

Iwatsuki et al.

[11] Patent Number: 5,064,057

[45] Date of Patent: Nov. 12, 1991

[54] SUPPORT FOR ANASTOMOSING OR CONNECTING LIVING ORGANS

[75] Inventors: Makoto Iwatsuki, Yokosuka; Toshio Hayashi, Kyoto, both of Japan

[73] Assignee: Ajinomoto Co., Inc., Tokyo, Japan

[21] Appl. No.: 501,363

[22] Filed: Mar. 30, 1990

Related U.S. Application Data

[63] Continuation of Ser. No. 187,461, Apr. 28, 1988, abandoned.

[30] Foreign Application Priority Data

Apr. 30, 1987 [JP] Japan ................................. 62-107125
Feb. 16, 1988 [JP] Japan ................................. 63-33505

[51] Int. Cl.$^5$ .......................... A61B 17/04; A61F 2/04
[52] U.S. Cl. ........................................ 606/154; 623/12
[58] Field of Search ................. 606/154, 153, 152, 151

[56] References Cited

U.S. PATENT DOCUMENTS

| | | | |
|---|---|---|---|
| 3,155,095 | 11/1964 | Brown | 606/154 |
| 3,683,926 | 8/1972 | Suzuki | 128/334 R |
| 3,975,350 | 8/1976 | Hudgin et al. | 623/1 X |
| 4,074,366 | 2/1978 | Capozza | 424/180 |
| 4,705,039 | 11/1987 | Sakaguchi et al. | 606/154 |

FOREIGN PATENT DOCUMENTS 0154103 11/1984 European Pat. Off. .
0194192  2/1986 European Pat. Off. .

*Primary Examiner*—David J. Isabella
*Assistant Examiner*—Debra S. Brittingham
*Attorney, Agent, or Firm*—Oblon, Spivak, McClelland, Maier & Neustadt

[57] ABSTRACT

Disclosed herein is a support for anastomosing or connecting living organs in a living body which comprises a material selected from the group consisting of monosaccharide, oligosaccharide, polysaccharide, a mixture thereof, and polyvinyl pyrrolidone.

The support provided according to the present invention has high safety and adaptability to the living body and is quickly dissolved away in body fluid in the living body, so that it can serve as an excellent support for a living tissue or organ in an anastomosing or connecting operation in a living body. This support assures secure anastomosis or connection and facilitates the surgical operations therefore.

8 Claims, No Drawings

SUPPORT FOR ANASTOMOSING OR CONNECTING LIVING ORGANS

This application is a continuation of application Ser. No. 187,461, filed on Apr. 28, 1988, now abandoned.

BACKGROUND OF THE INVENTION

The present invention relates to a novel support for anastomosing or connecting living organs. More particularly, the present invention relates to a support with high safety which can be used as a support for a living tissue in anastomosing or connecting living organs in a living body and which eliminates the need for being taken out after the surgery but is quickly dissolved away in body fluid in the living body.

A support is seldom used in anastomosing or connecting living organs, especially when sutures are performed. However, a support is often utilized when an adhesive is employed for anastomosing and connecting. For instance, in the case of skin adhesion, as is commonly practiced, the incised wound is first properly closed by the operator's fingers or by using a support and/or other instruments, then a piece of cloth made of polyethylene terephthalate or such cut to a width of 1.5 cm and a length slightly greater than the length of the wound is placed on the wound surface and an adhesive is dropped thereonto for effecting desired skin adhesion.

There are known the cases, although experimental ones, using a support tube for adhesion of blood vessels, in which a support tube made of a synthetic polymer such as polyglycolic acid which is decomposed in living body is inserted into the two ends of the blood vessels to be connected, and an adhesive is applied to the adherend end surfaces of the blood vessels for connecting them.

In the case of suture, if it becomes possible to use a support which can be inserted into tubular organs such as blood vessels, digestive organs, glands, etc., at the time of anastomosing or connecting these organs, the portion to be sutured will be stabilized in form, allowing secure and quick prosecutation of desired suture. In the actual surgerys, however, because of fine site of operation, a long time will be needed and also a highly expert hands of the operator will be required.

In order to solve these problems and to facilitate the surgery, use of an adhesive instead of suture has been proposed. In case of using an adhesive, the necessity for a support increases. When a tubular support is used in an organ in a living body, however, such support can not be taken out after the surgery, so that such support must be the one which is easily dissolved in body fluid in the organ. Especially in the case of blood vessels, thrombosis tends to occur around extraneous bodies when exist in the blood vessel, so that it is essential that the support must be dissolved away promptly. The in vivo decomposable polymers such as polyglycolic acid mentioned above are very slow to dissolve and therefore have a high probability of causing thrombosis. In order to prevent this, it has been attempted to treat the surface of the support contacted with blood with an antithrombotic agent, but no successful case has ever been reported.

Thus, there has been growing request for the development of a support which can be inserted into a tubular organ in a living body at the time of anastomosis or connection thereof to serve as a support for a living tissue and which eliminates the need for being taken out from the blood vessels after the surgery but is quickly dissolved away in body fluid in the organ, and moreover, is highly safe in use.

As a result of the studies on how to solve said problems, the present inventors found that a support made of a monosaccharide, oligosaccharide, polysaccharide, a mixture thereof or polyvinyl pyrrolidone could achieve the above-described aim and also easy to form, and the present invention has been achieved base on this finding.

SUMMARY OF THE INVENTION

In an aspect of the present invention, there is provided a support for anastomosing or connecting living organs in a living body which comprises a material selected from the group consisting of monosaccharide, oligosaccharide, polysaccharide, a mixture thereof, and polyvinyl pyrrolidone.

DETAILED DESCRIPTION OF THE INVENTION

The support for anastomosis or connection according to the present invention is characterized in that it is produced from a material selected from monosaccharide, oligosaccharide, polysaccharide, a mixture thereof, a polyvinyl pyrrolidone.

Many of the monosaccharide, oligosaccharide and polysaccharide, a mixture thereof and polyvinyl pyrrolidone usable in the present invention have the following properties: (1) they are easily soluble in water, eliminate the need for being taken out from the tubular organ after surgery and disappears before thrombosis occurs; (2) they are utilized as a sweetener or as a vehicle or excipient for principal foods or pharmaceuticals and are highly safe in use.

The monosaccharide and oligosaccharide are crystalline and melted on heating, so that they can be cast into a desired shape. Polysaccharide and polyvinyl pyrrolidone are the amorphous polymers which are not melted by heating, but they can be reduced to a viscous solution or a paste-like substance with water and can be formed into a desired shape by molding and drying or by coagulating in a non-aqueous solvent such as alcohol.

Further, the mixture of monosaccharide and polysaccharide, oligosaccharide and polysaccharide, and monosaccharide, oligosaccharide and polysaccharide have the following merits: (1) The frailness of monosaccharide and oligosaccharide and the mixture thereof due to their high crystallinity is compensated by the polymeric properties of polysaccharide. (2) Said mixtures necessarily containing a polysaccharide, when heated above the melting points of monosaccharide, oligosaccharide and mixtures thereof, are melted and turned into a syrup-like viscous substance even in the absence of water, and such viscous substance can be solidified by cooling, this process being reversible.

The present invention has been completed on the basis of said findings.

The monosaccharides usable in the present invention are represented by the general formula: $C_nH_{2n}O_n$ ($n=3$ to 10) and classified into triose, tetrose, pentose, hexose, heptose, octose, nonose and decose according to the number of n. Glucose and fructose are typical examples for hexose. They are admitted to be used as an injection medicine and no problem on safety arises when dissolved in blood in a blood vessel. Thus, they are recommended for use as most preferred monosaccharides in the present invention.

The monosaccharide derivatives, for example, saccharic acids such as gluconic acid formed by oxidizing glucose and sugar alcohols such as D-sorbitol and D-mannitol formed by reducing glucose, and xylitol formed by reducing xylose, etc., are also included in the scope of the monosaccharide in the present invention. Especially D-sorbitol, D-mannitol and xylitol are preferable for use in the present invention as they are stable even when melted by heating, cause no browning reaction peculiar to the sugars and are pharmacologically accepted as a component of injection medicines.

Oligosaccharides are divided into di- to decasaccharides according to the molecular number of monosaccharides produced from hydrolysis. Disaccharides such as maltose, lactose and sucrose and trisaccharides such as raffinose and melezitose are used as a food component and can be cited as preferred oligosaccharides with high safety for use in the present invention.

Polysaccharides usable in the present invention are the nutritive polysaccharides such as starch, glycogen, dextran, pullulan, inulin, etc., and their derivatives such as hydroxyethyl starch. Among them, hydroxyethyl starch and dextran are commonly used as a blood bulking agent and preferred for use in the present invention as they are very high in safety when used as a support for blood vessels.

In case of using a mixture of two or more of monosaccharides, oligosaccharides and polysaccharides, their mixing ratio depends on shape, size and region of use of the support and is not restricted in the present invention.

For example, in the case of a mixture of a monosaccharide and a polysaccharide, the greater mixing ratio of the monosaccharide shows a tendency to lower the viscosity of the molten mixture and, consequently, the shaped product obtained therefrom becomes more hard and frail, while the solubility in body fluid increases. Therefore, the mixing ratios of the materials may be properly selected according to other conditions such as thickness, shape and size of the support to be made and the region of use thereof.

For producing the support, in case of using a monosaccharide, an oligosaccharide or a mixture thereof as a starting material, since these saccharides can be melted by heating as mentioned above, there can be used the same techniques as generally employed for producing glass tubes or glass plates from molten glass, or may be molded into a desired shape such as tube, semicylinder, plate, etc.

In the case of using polysaccharides or polyvinyl pyrrolidone as the starting material, desired molding can be accomplished by forming a syrup-like substance with water, followed by casting and drying, or by coagulating such a syrup-like substance in a non-aqueous solvent.

In the case of using a mixture of monosaccharide and polysaccharides, oligosaccharide and polysaccharides, or monosaccharide, oligosaccharide and polysaccharides as the starting material, since such mixture can be melted and turned into a syrup-like viscous substance when heated above the melting points of said monosaccharide and oligosaccharides or mixture thereof even in the absence of water, there can be used the same techniques as employed for producing glass tubes or glass plates from molten glass, or casting method.

In any case, molding can be repeated by melting the once formed support by heating and re-molding it, and the support of a desired shape and size can be easily produced.

The support molded from said materials without using water is usually hard and frail, so that care is needed for handling and storage thereof. For the purpose of reinforcement, a substance assured for high safety and having a plasticizing effect, such as water, may be previously added in the material or may be left in the support when dried. If necessary, various kinds of pharmaceutical compounds may be also added similarly to said plasticizing substance.

For retarding dissolution of the support in body fluid, a substance which is sparingly soluble in water and causes no ill effect to the living body when mixed in body fluid may be blended in the support in the course of its molding or coated on the surface thereof.

The support for anastomosing or connecting living organs in a living body according to the present invention can be shaped into a desired form such as tube, semicylinder, plate, etc., but the tubular form is most suited for practical use. The dimentional conditions such as the length, thickness, etc. of the support may be selected according to the ordinary skill of the art.

The present invention will be described more precisely while referring to the following non-limitative Examples.

EXAMPLE 1

Molding of support

Japanese pharmacopoeia glucose, fructose, D-sorbitol and xylitol were selected for use as monosaccharide and non Japanese pharmacopoeia hydroxyethyl starch (HES) and dextran 40 were selected for use as polysaccharide. The monosaccharide and the polysaccharide shown in Table 1 were mixed (50 parts by weight each) in a glass container.

The inside atmosphere of the container was replaced with nitrogen and the mixture was gradually heated in an oil bath. When a temperature above the melting point of monosaccharide was reached, the polysaccharide was also melted and the mixture was reduced into a syrup-like melt.

According to the manner of forming a fine glass tube from molten glass, an end of a glass tube was introduced into the syrup-like melt, then taken out and quickly stretched to form a tube having an outer diameter of about 4 mm and an inner diameter of about 2 mm. The tube was cut to a length of 10 mm and kept in a container having a desiccant placed therein.

The results are shown in Table 1.

TABLE 1

| No. | Monosaccharide | Polysaccharide | |
|---|---|---|---|
| 1 | Glucose | HES | Brown |
| 2 | Glucose | Dextran 40 | " |
| 3 | Fructose | HES | " |
| 4 | Fructose | Dextran 40 | " |
| 5 | D-sorbitol | HES | Colorless |
| 6 | D-sorbitol | Dextran 40 | " |
| 7 | Xylitol | HES | " |
| 8 | Xylitol | Dextran 40 | " |

EXAMPLE 2

Solubility of support

In order to confirm that the support is dissolved away in a short period of time (preferably in less than 10 minutes), the following test was carried out.

Silicone tubes were connected by using the supports obtained in Example 1, and then the various types of fluid shown in Table 2, each being maintained at 37.5° C., were circulated through the connected tubes at a flow rate of about 200 ml/min by using a roller pump (mfd. by Furue Science Co., Ltd.) The state of dissolution of the support was observed while determining the time required till the support was dissolved away.

The results are shown in Table 2.

In each case, the support was dissolved away in a short period of time. It was observed that the tubular support was dissolved gradually from the inside, and there took place no break of the support in the silicone tube nor obstruction of the tube by the support in the course of fluid circulation.

TABLE 2

| No. | Circulating fluid | Support No. (Example 1) | Time required till support was dissolved away |
|---|---|---|---|
| 1 | Ringer's solution* | 1 | 6'36" |
| 2 | Ringer's solution* | 2 | 6'56" |
| 3 | Ringer's solution* | 3 | 6'15" |
| 4 | Ringer's Pharmacopoeia. | 4 | 7'06" |
| 5 | Ringer's solution* | 5 | 6'24" |
| 6 | Ringer's solution* | 6 | 7'13" |
| 7 | Ringer's solution* | 7 | 5'58" |
| 8 | Ringer's solution* | 8 | 6'46" |
| 9 | Dextran 70 injection* | 1 | 7'14" |
| 10 | Dextran 70 injection* | 2 | 6'42" |
| 11 | Dextran 70 injection* | 3 | 6'37" |
| 12 | Dextran 70 injection* | 4 | 7'02" |
| 13 | Dextran 70 injection* | 5 | 5'49" |
| 14 | Dextran 70 injection* | 6 | 6'39" |
| 15 | Dextran 70 injection* | 7 | 6'26" |
| 16 | Dextran 70 injection* | 8 | 7'25" |
| 17 | Fresh blood of dog | 1 | 7'20" |
| 18 | Fresh blood of dog | 2 | 6'58" |
| 19 | Fresh blood of dog | 3 | 7'16" |
| 20 | Fresh blood of dog | 4 | 7'43" |
| 21 | Fresh blood of dog | 5 | 6'45" |
| 22 | Fresh blood of dog | 6 | 7'23" |
| 23 | Fresh blood of dog | 7 | 6'57" |
| 24 | Fresh blood of dog | 8 | 7'52" |

*Prepared according to Japanese Pharmacopeia.

EXAMPLE 3

Retardation of dissolution of support

One g of non Japanese pharmacopoeia purified yolk lecithin was dissolved in 10 ml of chloroform, and the tubular supports produced in Example 1 were immersed in this solution. One minute later, the tubular supports were taken out and dried in vacuo.

The solubility of the supports coated with said purified yolk lecithin was examined comparatively according to the test methods of No. 5 and No. 21 in Example 2. The results show that the time required for the support to be dissolved away was greatly prolonged: 9'31" in the case of the method of No. 5 and 10'05" in the case of the method of No. 21.

As in Example 2, the tubular support was dissolved gradually from the inside, and there took place no break of the support in the silicone tube nor obstruction of the tube in the course of the operation.

Further, as a secondary effect, the influece of humidity in the air on the tubular support could be lessened. The non-coated support was very hygroscopic and required care for its handling and storage, but the coated support had no stickiness on the surface even if left in the air.

What is claimed is:

1. An anastomosing support for anastomosing or connecting organs in a living body, said support consisting essentially of a mixture of a monosaccharide and a polysaccharide, wherein said mixture dissolves in said living body in less than 10 minutes but more than a couple of minutes.

2. The support of claim 1, wherein said polysaccharide is selected from the group consisting of dextran and hydroxyethyl starch.

3. The support of claim 1, wherein said polysaccharide is dextran.

4. The support of claim 1, wherein said polysaccharide is hydroxyethyl starch.

5. The support of claim 1, wherein said monosaccharide is selected from the group consisting of glucose, fructose, gluconic acid, D-sorbitol, D-mannitol and xylitol.

6. The support of claim 1, wherein said support is tubular in shape.

7. The support of claim 1, wherein said polysaccharide is selected from the group consisting of starch, glycogen, dextran, pullulan, inulin and hydroxyethyl starch.

8. The support of claim 1, wherein said mixture is soluble in water.

* * * * *